United States Patent
Leker et al.

(10) Patent No.: US 9,908,832 B2
(45) Date of Patent: Mar. 6, 2018

(54) DECARBOXYLATION OF CANNABIDIOLIC ACID IN HEMP BIOMASS AND HEMP EXTRACT

(71) Applicant: S.S. STEINER, INC., New York, NY (US)

(72) Inventors: Jeremy Leker, Yakima, WA (US); John Paul Maye, Great Falls, VA (US)

(73) Assignee: S.S. STEINER, INC., New York, NY (US)

( * ) Notice: Subject to any disclaimer, the term of this patent is extended or adjusted under 35 U.S.C. 154(b) by 0 days.

(21) Appl. No.: 15/633,555

(22) Filed: Jun. 26, 2017

(65) Prior Publication Data

US 2018/0016216 A1    Jan. 18, 2018

Related U.S. Application Data

(60) Provisional application No. 62/362,806, filed on Jul. 15, 2016.

(51) Int. Cl.
*C07C 37/50*    (2006.01)

(52) U.S. Cl.
CPC .......... *C07C 37/50* (2013.01); *C07C 2601/16* (2017.05)

(58) Field of Classification Search
CPC ....................................... C07C 37/50
USPC ........................................... 549/389
See application file for complete search history.

(56) References Cited

U.S. PATENT DOCUMENTS

| 7,344,736 B2 | 3/2008 | Whittle et al. ................. 424/725 |
| 2015/0038567 A1 | 2/2015 | Herkenroth et al. ......... 514/454 |

OTHER PUBLICATIONS

International Search Report issued in application No. PCT/US17/39310, dated Sep. 25, 2017 (8 pgs).

*Primary Examiner* — Taofiq A Solola
(74) *Attorney, Agent, or Firm* — Hayes Soloway P.C.

(57) ABSTRACT

Provided is a decarboxylating carboxylic acids of cannabinoids in hemp extract or hemp biomass in which the hemp extract or hemp biomass is heated to a temperature of 40° C. to 100° C. in the presence of one or more divalent or monovalent reagents.

15 Claims, No Drawings

DECARBOXYLATION OF CANNABIDIOLIC ACID IN HEMP BIOMASS AND HEMP EXTRACT

CROSS REFERENCE TO RELATED APPLICATIONS

This application claims priority from U.S. Provisional Application Ser. No. 62/362,806, filed Jul. 15, 2016, the contents of which are incorporated herein by reference.

BACKGROUND

Industrial hemp which contains little to no psychoactive compounds like Tetrandryocannabinol (THC) has many uses. The seeds can make up as much as half of the weight of the whole plant and about ⅓ of the seed weight is composed of hemp oil, which is rich in omega-3 fatty acids and ¼ by weight protein. The oil and whole seeds are used as a dietary supplement. The outside part of the stalk or fiber of the plant can be used to make rope, paper, and fiberboard. The stalk contains Cannabidiolic Acid (CBDa) in concentrations as low as 1-6% with some experimental varieties containing more. CBDa has little to no medicinal properties whereas its decarboxylated counterpart Cannabidiol (CBD) has many. CBDa can be decarboxylated to make CBD. The most common methods for doing this is to first extract the hemp stalks (biomass) with a solvent like high pressure super critical CO2, liquid $CO_2$ or an organic solvent such as a lower (C1-C4) alcohol, e.g., methanol, ethanol, propanol or butanol. The resulting hemp extract can contain about 3% to 35% CBDa depending on the variety and this extract is typically heated to temperatures as high as 140° C. for several hours to decarboxylate the CBDa to form CBD. The conversion efficiency of this step is about 78-80% in the lab and 60-70% commercially. In order to reach these high temperatures, special heating equipment is required and the largest batch size for this heating equipment is typically quite small, around 200-kg.

There is a real need to be able to decarboxylate hemp extract at lower temperatures, 100° C. or less, and in larger batch sizes. Low temperature decarboxylation would not need any special heating equipment and could be performed in most industrial plants were heating with steam is common.

There is also a need to decarboxylate the CBDa in hemp biomass. If this could be done, then one could simply extract the biomass at low pressure liquid CO2 and collect the CBD without having to further process the hemp extract.

SUMMARY OF INVENTION

CBDa is an alkyl carboxylic acid. The chemical literature reports many chemical reagents that can be used to decarboxylate carboxylic acids, however, most are not food grade, most only work on pure compounds, and most still require very high temperatures. It was discovered that if one mixes food grade oxides like ZnO, MgO, CaO, or salts like $Na_2SO_4$ with powdered hemp biomass and heats the Biomass to 40° C. to 100° C., preferably 50° C. to 90° C., more preferably 60° C. to 75° C., within a few days the majority of the CBDa is converted to CBD. Interestingly if these reagents are added to $CO_2$ Hemp extract and heated to about 50° C., the decarboxylation can be completed within about 24 hours. It was also discovered that if one mixed the hemp extract with water, $MgSO_4$ and a small amount of caustic, like NaOH, and mixes and heats this mixture at to about 75° C. one can perform the decarboxylation within 2 hours. It was totally unexpected that one could decarboxylate a complex mixture like hemp biomass or $CO_2$ hemp extract by simply adding these reagents. It was even more unexpected that temperatures less than 100° C. could perform this decarboxylation.

In one aspect, the present invention provides a method for decarboxylating carboxylic acids of cannabinoids in hemp extract or hemp biomass which comprises heating the hemp extract or hemp biomass to a temperature of 40° C. to 100° C. in the presence of one or more divalent or monovalent reagents. In such aspect the carboxilyc acids of cannabinoids are selected from the group consisting of cannabidolic acid, tetrahydrocannabonolic acid, and mixtures thereof.

In another aspect of the invention the hemp extract comprises a super critical $CO_2$ extract or a Liquid $CO_2$ extract of hemp or a hemp biomass.

In yet another aspect of the invention the hemp extract comprises an organic solvent extract of hemp or a hemp biomass, wherein the organic solvent extract preferably comprises an alcohol extract or a hexane extract of hemp or a hemp biomass, more preferably a lower alcohol selected from the group consisting of methanol, ethanol, propanol and butanol.

In yet another aspect of the invention, the reagent used to perform the decarboxylation is selected from the group consisting of a divalent metal oxide, a divalent metal hydroxide, and divalent metal salts, and a mixture thereof, preferably MgO, CaO, ZnO, $Mg(OH)_2$, $Ca(OH)_2$, $CaCl_2$, $MgSO4$, $MgSO4(H_2O)_7$, and $ZnSO4$ and a mixture thereof, or, a sodium, a potassium and a lithium monovalent salt or hydroxide, and a mixture thereof, preferably $Na_2SO_4$, $K_2SO_4$, $Li_2SO_4$, NaOH, KOH, and LiOH, and a mixture thereof.

In still yet another aspect of the invention, the temperature is from is 50° C. to 80° C., preferably from 60° C. to 75° C.

In yet another aspect of the invention the hemp extract or hemp biomass is heated in the presence of one or more divalent or monovalent reagents and water, or the hemp extract or hemp biomass is heated in the presence of one or more divalent or monovalent reagents in the absence of water.

EXPERIMENTS 200.0 g of super critical $CO_2$ hemp extract was mixed with 2 wt. % of ZnO, or MgO, or CaO at 50° C. until the powder was evenly mixed into the extract. The extract mixture was placed in a 50° C. oven and at ambient temperature. The three extract mixtures were also used to make a mixed oxide sample with 2 wt % 1:1:1 ZnO:MgO:CaO, which was also placed in the 50° C. oven and ambient. A control extract and pellet sample were also placed in the 50° C. oven. High Performance Liquid Chromatography, HPLC, analysis was performed by adding 0.5 grams of the hemp extract to a 50 mL volumetric flask. 20 mL of isopropyl alcohol was sonicated with the extract to completely dissolve it and then made up to volume with methanol. The sample was diluted 1:10 in acidic methanol for HPLC analysis. See results in Table 1.

TABLE 1

HPLC Results of Hemp Extract with and without Treatment

| Treatment | Temp (° C.) | Time (Days) | CBD (%) | CBDA (%) | Conversion (%) | Yield (%) |
|---|---|---|---|---|---|---|
| Extract | | 0 | 1.38 | 3.20 | 0.0 | 100.0 |
| Extract | 50 | 7 | 1.33 | 2.97 | 7.2 | 94.0 |
| Extract w/2% ZnO | 50 | 1 | 3.55 | 0.70 | 78.2 | 92.8 |
| Extract w/2% MgO | 50 | 1 | 3.02 | 1.21 | 62.3 | 92.2 |
| Extract w/2% CaO | 50 | 1 | 3.10 | 1.15 | 64.0 | 92.7 |
| Extract w/2% CaO:ZnO:MgO | 50 | 1 | 2.63 | 1.69 | 47.1 | 94.4 |

In a second experiment 90.0 g of hemp extract was mixed with 210 g of RO water and $MgSO_4(H_2O)_7$ (epsum salts) so that the Mg:CBDA mol ratio was 1:1 or 2:1. The mixture was stirred and brought up to a temperature of 50° C. After the temperature was achieved 50% NaOH was added to achieve a pH of 6.7 at 50° C. Aliquots of resin were taken at various intervals and analyzed by HPLC. HPLC analysis was conducted by adding 0.5 grams of hemp extract to a 50 mL volumetric flask. 20 mL of isopropyl alcohol was sonicated with the extract to completely dissolve it and then made up to volume with methanol. The sample was diluted 1:10 in acidic methanol for HPLC analysis. See table 2.

TABLE 2

Aqueous Decarboxylation of Hemp Extract with MgSO4 and NaOH

| MgSO4 (mol) | NaOH (mol) | pH @ 50° C. | Temp (° C.) | Time (min) | CBD (%) | CBDA (%) | Total (%) | Decarboxylation (%) |
|---|---|---|---|---|---|---|---|---|
| control | | | | | 1.60 | 3.20 | 4.80 | 33.3 |
| 1.0 | 1.0 | 6.71 | 75 | 0 | 1.46 | 2.33 | 3.79 | 38.6 |
| | | | | 30 | 3.18 | 1.92 | 5.10 | 62.4 |
| | | | | 68 | 4.02 | 1.06 | 5.07 | 79.2 |
| | | | | 90 | 4.30 | 0.71 | 5.01 | 85.9 |
| | | | | 150 | 4.22 | 0.14 | 4.36 | 96.7 |
| | | | | 240 | 4.85 | 0.02 | 4.87 | 99.6 |
| control | | | | 0 | 1.60 | 3.20 | 4.80 | 33.3 |
| 2.0 | 1.36 | 6.74 | 75 | 30 | 2.51 | 2.45 | 4.96 | 50.6 |
| | | | | 65 | 4.03 | 1.27 | 5.30 | 76.1 |
| | | | | 100 | 4.04 | 0.42 | 4.46 | 90.6 |
| | | | | 130 | 3.60 | 0.16 | 3.76 | 95.7 |
| | | | | 150 | 4.69 | 0.12 | 4.81 | 97.5 |
| 2.0 | 1.36 | 6.74 | 85 | 0 | 1.60 | 3.20 | 4.80 | 33.3 |
| | | | | 30 | 4.15 | 0.59 | 4.75 | 87.5 |
| | | | | 60 | 4.68 | 0.07 | 4.76 | 98.5 |
| | | | | 90 | 4.80 | 0.01 | 4.81 | 99.9 |

In a third set of experiments, hemp biomass was mixed with the below reagents, placed into a vacuum foil and heated for 5 days at 50° C. to perform the decarboxylation. As table 3 shows, these reagents more efficiently increase the yield of CBD and rate of CBDa decarboxylation.

TABLE 3

Decarboxylation of Hemp Biomass in Vacuum Packs

| Treatment | Temp (° C.) | Days | CBD (%) | CBDA (%) | DC Ratio (%) | Yield (%) |
|---|---|---|---|---|---|---|
| Control | | 0.0 | 0.06 | 1.07 | 5.1 | 100.0 |
| | 50 | 5 | 0.58 | 0.21 | 73.9 | 69.9 |
| 1% MgO 0% | | 0.0 | 0.05 | 0.99 | 5.2 | 100.0 |
| Na2SO4 | 50 | 5 | 0.73 | 0.18 | 80.1 | 86.8 |
| 2% MgO 0% | | 0.0 | 0.08 | 1.00 | 7.1 | 100.0 |
| Na2SO4 | 50 | 5 | 0.68 | 0.16 | 81.0 | 77.8 |
| 0% MgO 1% | | 0.0 | 0.06 | 1.07 | 5.1 | 100.0 |
| Na2SO4 | 50 | 5 | 0.77 | 0.13 | 85.8 | 79.9 |
| 0% MgO 2% | | 0.0 | 0.06 | 1.07 | 5.1 | 100.0 |
| Na2SO4 | 50 | 5 | 0.54 | 0.42 | 56.7 | 85.1 |
| 1% MgO 1% | | 0.0 | 0.05 | 0.99 | 5.2 | 100.0 |
| Na2SO4 | 50 | 5 | 0.71 | 0.23 | 75.2 | 89.7 |
| 2% MgO 1% | | 0.0 | 0.08 | 1.00 | 7.1 | 100.0 |
| Na2SO4 | 50 | 5 | 0.57 | 0.29 | 66.7 | 79.7 |
| 1% Mg0 2% | | 0.0 | 0.05 | 0.99 | 5.2 | 100.0 |
| Na2SO4 | 50 | 5.0 | 0.55 | 0.37 | 60.0 | 87.6 |
| 2% MgO 2% | | 0.0 | 0.08 | 1.00 | 7.1 | 100.0 |
| Na2SO4 | 50 | 5 | 0.75 | 0.11 | 86.8 | 79.8 |

In a fourth experiment, to demonstrate the large scale processing capabilities of this invention, 3000-kg of $CO_2$ Hemp Extract was mixed with 6000-kg of water, and one mole equivalent of MgSO4 and NaOH and heated for two hours at 75° C. The conversion yield and isolation yields were both 86.9%, see table 4.

TABLE 4

| | Mass (kg) | CBD (%) | CBDa (%) | Active Yield (%) |
|---|---|---|---|---|
| CO2 Hemp Extract | 3000 | 2.50 | 4.27 | 100 |
| End of Decarboxylation | 2902 | 6.08 | 0.01 | 86.9 |

Some hemp extract contains small concentration of tetrahydrocannabinolic acid, THCa. It was noticed that this decarboxylation process can also be used to decarboxylate THCa to make the psychoactive cannabinoid tetrahydrocannabinol, THC. To 100 grams of hemp extract was added 200 grams of water, heated to 85° C., and added 1 mol MgSO4 and 0.98 mol of NaOH. The results and yield of the decarboxylation are shown on Table 5.

TABLE 5

Decarboxylation of THCa to make THC

| Time (min) | THC (%) | THCa (%) | Conversion (%) |
|---|---|---|---|
| 0 | 0.30 | 0.99 | 25.68 |
| 13 | 0.77 | 0.03 | 97.12 |
| 30 | 0.72 | 0.02 | 97.64 |
| 62 | 0.68 | 0.01 | 98.99 |
| 90 | 0.69 | 0.03 | 96.58 |

What is claimed:

1. A method for decarboxylating carboxylic acids of cannabinoids in hemp extract or hemp biomass which comprises heating the hemp extract or hemp biomass to a temperature of 40° C. to 100° C. in the presence of one or more divalent or monovalent reagents.

2. The method of claim 1, wherein the carboxylic acids of cannabinoids are selected from the group consisting of cannabidolic acid, tetrahydrocannabonolic acid, and mixtures thereof.

3. The method of claim 1, wherein the hemp extract comprises a super critical $CO_2$ extract or a Liquid $CO_2$ extract of hemp or a hemp biomass.

4. The method of claim 1, wherein the hemp extract comprises an organic solvent extract of hemp or a hemp biomass.

5. The method of claim 4, wherein the organic solvent extract comprises an alcohol extract or a hexane extract of hemp or a hemp biomass.

6. The method of claim 5, wherein the alcohol comprises a lower alcohol selected from the group consisting of methanol, ethanol, propanol and butanol.

7. The method of claim 6, wherein the alcohol is ethanol.

8. The method of claim 1, wherein the reagent used to perform the decarboxylation is selected from the group consisting of a divalent metal oxide, a divalent metal hydroxide, and divalent metal salts, and a mixture thereof.

9. The method of claim 8, wherein the reagent is selected from the group consisting of MgO, CaO, ZnO, $Mg(OH)_2$, $Ca(OH)_2$, $CaCl_2$, $MgSO4$, $MgSO4(H_2O)_7$, and $ZnSO4$ and a mixture thereof.

10. The method of claim 1, wherein a reagent used to perform the decarboxylation is selected from the group consisting of a sodium, a potassium and a lithium monovalent salt or hydroxide, and a mixture thereof.

11. The method of claim 9, wherein the monovalent salt is selected from the group consisting of $Na_2SO_4$, $K_2SO_4$, $Li_2SO_4$, NaOH, KOH, and LiOH, and a mixture thereof.

12. The method of claim 1, wherein the temperature is from is 50° C. to 80° C.

13. The method of claim 1, wherein the temperature is from 60° C. to 75° C.

14. The method of claim 1, wherein the hemp extract of hemp biomass is heated in the presence of one or more divalent or monovalent reagents and water.

15. The method of claim 1, wherein the hemp extract or hemp biomass is heated in the presence of one or more divalent or monovalent reagents in the absence of water.

* * * * *